(12) United States Patent (10) Patent No.: US 9,333,290 B2
Rotem (45) Date of Patent: May 10, 2016

(54) ANTI-FREE FLOW MECHANISM

(75) Inventor: Shachar Rotem, M.P. Hefer (IL)

(73) Assignee: Q-CORE MEDICAL LTD., Netanya (IL)

( * ) Notice: Subject to any disclaimer, the term of this patent is extended or adjusted under 35 U.S.C. 154(b) by 195 days.

(21) Appl. No.: 12/514,311

(22) PCT Filed: Nov. 13, 2007

(86) PCT No.: PCT/IL2007/001405
§ 371 (c)(1),
(2), (4) Date: May 10, 2009

(87) PCT Pub. No.: WO2008/059499
PCT Pub. Date: May 22, 2008

(65) Prior Publication Data
US 2010/0036322 A1 Feb. 11, 2010

(30) Foreign Application Priority Data
Nov. 13, 2006 (IL) .......................................... 179234

(51) Int. Cl.
*A61M 5/142* (2006.01)
*A61M 39/28* (2006.01)

(52) U.S. Cl.
CPC ........... *A61M 5/14228* (2013.01); *A61M 5/142* (2013.01); *A61M 5/1424* (2013.01); *A61M 39/28* (2013.01); *A61M 2205/14* (2013.01); *A61M 2205/276* (2013.01)

(58) Field of Classification Search
CPC .......... A61M 5/1424; A61M 5/14232; A61M 5/1422; A61M 5/14228; A61M 5/142; F04B 43/021
USPC ................................ 604/153; 417/474–477.2
See application file for complete search history.

(56) References Cited

U.S. PATENT DOCUMENTS 2,056,322 A 10/1936 Hoppe
2,393,838 A * 1/1946 Tarbox .................. B01L 3/0241
152/415

(Continued)

FOREIGN PATENT DOCUMENTS

DE 10118086 A 7/2002
DE 10118086 A1 7/2002

(Continued)

OTHER PUBLICATIONS

U.S. Appl. No. 10/535,103 Official Action dated Feb. 2, 2009.

(Continued)

*Primary Examiner* — Andrew Gilbert
*Assistant Examiner* — Matthew A Engel
(74) *Attorney, Agent, or Firm* — Vladimir Sherman; Professional Patent Solutions

(57) ABSTRACT

The present invention discloses an anti-free flow mechanism for a finger-type peristaltic infusion pump (DDS) and methods for avoiding anti-free-flow. The mechanism comprises: a passive mechanical interface (MS) which integrally accommodates a portion of the flexible infusion tube, and an anti-free flow valve (AFFV) which is a spring-activated latch, which is incorporated within said MS. The maneuverable latch is secured in the MS either in CLOSED or OPEN configurations: in its CLOSED configuration no flow is provided, and in its OPEN configuration, a free flow is facilitated. Said anti-free flow mechanism is configured in a manner such that when the MS is not properly mounted in the DDS, said AFFV is automatically actuated via one or more integrated springs, to its CLOSED configuration. When the MS is properly mounted in the DDS, said latch is adapted to be automatically switched to the OPEN configuration.

2 Claims, 4 Drawing Sheets

(56) References Cited

U.S. PATENT DOCUMENTS

| | | | |
|---|---|---|---|
| 2,743,898 A | 5/1956 | King | |
| 2,981,115 A | 4/1961 | Beguin | |
| 3,443,585 A | 5/1969 | Reinicke | |
| 3,511,583 A | 5/1970 | Brown | |
| 3,677,667 A | 7/1972 | Morrison | |
| 3,778,195 A | 12/1973 | Bamberg | |
| 3,982,722 A | 9/1976 | Bernard | |
| 3,982,725 A | 9/1976 | Clark | |
| 4,014,318 A | 3/1977 | Dockum et al. | |
| 4,039,269 A | 8/1977 | Pickering | |
| 4,155,362 A | 5/1979 | Jess | |
| 4,178,138 A | 12/1979 | Iles | |
| 4,236,880 A | 12/1980 | Archibald | |
| 4,270,532 A | 6/1981 | Franetzki et al. | |
| 4,290,346 A | 9/1981 | Bujan | |
| 4,320,781 A | 3/1982 | Bouvet et al. | |
| 4,373,525 A | 2/1983 | Kobayashi | |
| 4,450,375 A | 5/1984 | Siegal | |
| 4,460,358 A * | 7/1984 | Somerville | A61M 5/16813 128/DIG. 13 |
| 4,479,797 A | 10/1984 | Kobayashi et al. | |
| 4,489,863 A | 12/1984 | Horchos et al. | |
| 4,493,706 A * | 1/1985 | Borsanyi | A61M 5/142 128/DIG. 12 |
| 4,650,469 A | 3/1987 | Berg et al. | |
| 4,671,792 A * | 6/1987 | Borsanyi | F04B 43/082 128/DIG. 12 |
| 4,682,135 A | 7/1987 | Yamakawa | |
| 4,689,043 A * | 8/1987 | Bisha | A61M 5/142 128/DIG. 13 |
| 4,690,673 A | 9/1987 | Bloomquist | |
| 4,725,205 A * | 2/1988 | Cannon | F04B 43/021 417/363 |
| 4,728,265 A * | 3/1988 | Cannon | A61M 5/14228 16/225 |
| 4,741,736 A | 5/1988 | Brown | |
| 4,748,003 A | 5/1988 | Riley | |
| 4,755,168 A | 7/1988 | Romanelli et al. | |
| 4,836,752 A | 6/1989 | Burkett | |
| 4,857,048 A * | 8/1989 | Simons | A61M 5/14224 417/26 |
| 4,867,744 A | 9/1989 | Borsanyi | |
| 4,893,991 A * | 1/1990 | Heminway | F04B 43/082 417/474 |
| 4,927,411 A | 5/1990 | Pastrone et al. | |
| 4,954,046 A * | 9/1990 | Irvin | A61M 5/14228 128/DIG. 12 |
| 4,954,256 A | 9/1990 | Degen et al. | |
| 4,978,335 A | 12/1990 | Arthur, III | |
| 5,074,756 A | 12/1991 | Davis | |
| 5,078,683 A | 1/1992 | Sancoff et al. | |
| 5,088,904 A * | 2/1992 | Okada | F04B 43/082 417/474 |
| 5,096,385 A | 3/1992 | Georgi et al. | |
| 5,103,211 A | 4/1992 | Daoud et al. | |
| 5,151,019 A | 9/1992 | Danby et al. | |
| 5,152,680 A | 10/1992 | Okada | |
| 5,165,874 A | 11/1992 | Sancoff et al. | |
| 5,213,483 A | 5/1993 | Flaherty et al. | |
| 5,219,327 A | 6/1993 | Okada | |
| 5,222,946 A | 6/1993 | Kamen | |
| 5,246,347 A | 9/1993 | Davis | |
| 5,257,978 A * | 11/1993 | Haber | A61M 39/281 251/9 |
| 5,286,176 A | 2/1994 | Bonin | |
| 5,290,158 A * | 3/1994 | Okada | A61M 5/142 417/474 |
| 5,308,333 A | 5/1994 | Skakoon | |
| 5,338,157 A | 8/1994 | Blomquist | |
| 5,395,320 A | 3/1995 | Padda et al. | |
| 5,429,485 A | 7/1995 | Dodge | |
| 5,485,408 A | 1/1996 | Blomquist | |
| 5,499,969 A | 3/1996 | Beuchat et al. | |
| 5,509,439 A | 4/1996 | Tantardini | |
| 5,527,295 A | 6/1996 | Wing | |
| 5,542,826 A * | 8/1996 | Warner | A61M 5/14228 417/474 |
| 5,569,188 A | 10/1996 | Mackool | |
| 5,575,309 A | 11/1996 | Connell | |
| 5,575,631 A | 11/1996 | Jester | |
| 5,577,891 A * | 11/1996 | Loughnane | F04B 43/082 417/412 |
| 5,584,667 A | 12/1996 | Davis | |
| 5,593,134 A | 1/1997 | Steber et al. | |
| 5,601,420 A | 2/1997 | Warner et al. | |
| 5,628,619 A | 5/1997 | Wilson | |
| 5,658,250 A | 8/1997 | Blomquist et al. | |
| 5,658,252 A | 8/1997 | Johnson | |
| 5,660,529 A | 8/1997 | Hill | |
| 5,669,877 A | 9/1997 | Blomquist | |
| 5,683,233 A | 11/1997 | Moubayed et al. | |
| 5,695,473 A | 12/1997 | Olsen | |
| 5,704,584 A | 1/1998 | Winterer et al. | |
| 5,742,519 A | 4/1998 | McClendon et al. | |
| 5,782,805 A | 7/1998 | Meinzer et al. | |
| 5,788,669 A | 8/1998 | Peterson | |
| 5,791,880 A | 8/1998 | Wilson | |
| 5,791,881 A | 8/1998 | Moubayed et al. | |
| 5,803,712 A | 9/1998 | Davis et al. | |
| 5,807,322 A | 9/1998 | Lindsey et al. | |
| 5,810,323 A | 9/1998 | Winterer et al. | |
| 5,853,386 A | 12/1998 | Davis et al. | |
| 5,876,370 A | 3/1999 | Blomquist | |
| 5,888,052 A | 3/1999 | Hill | |
| 5,896,076 A | 4/1999 | Van Namen | |
| 5,909,724 A | 6/1999 | Nishimura et al. | |
| 5,924,852 A | 7/1999 | Moubayed et al. | |
| 5,935,099 A | 8/1999 | Peterson et al. | |
| 5,935,106 A | 8/1999 | Olsen | |
| 5,943,633 A | 8/1999 | Wilson et al. | |
| 5,954,485 A | 9/1999 | Johnson et al. | |
| 5,980,490 A | 11/1999 | Tsoukalis | |
| 5,996,964 A | 12/1999 | Ben-Shalom | |
| 6,024,539 A | 2/2000 | Blomquist | |
| 6,095,189 A | 8/2000 | Ben-Shalom | |
| 6,110,153 A | 8/2000 | Davis et al. | |
| 6,117,115 A * | 9/2000 | Hill | A61M 5/16813 604/250 |
| 6,146,109 A | 11/2000 | Davis et al. | |
| 6,164,921 A | 12/2000 | Moubayed et al. | |
| 6,165,874 A | 12/2000 | Powell et al. | |
| RE37,074 E | 2/2001 | Danby et al. | |
| 6,203,296 B1 | 3/2001 | Ray et al. | |
| 6,213,723 B1 | 4/2001 | Danby et al. | |
| 6,213,739 B1 * | 4/2001 | Phallen | F04B 13/02 417/474 |
| 6,234,773 B1 * | 5/2001 | Hill | A61M 5/14228 417/474 |
| 6,241,704 B1 | 6/2001 | Peterson et al. | |
| 6,261,262 B1 | 7/2001 | Briggs et al. | |
| 6,280,408 B1 | 8/2001 | Sipin | |
| 6,312,227 B1 | 11/2001 | Davis | |
| 6,339,410 B1 | 1/2002 | Milner et al. | |
| 6,347,553 B1 | 2/2002 | Morris et al. | |
| 6,371,732 B1 | 4/2002 | Moubayed et al. | |
| 6,422,057 B1 | 7/2002 | Anderson | |
| 6,450,773 B1 | 9/2002 | Upton | |
| 6,475,180 B2 | 11/2002 | Peterson et al. | |
| 6,519,569 B1 | 2/2003 | White et al. | |
| 6,537,244 B2 | 3/2003 | Paukovits et al. | |
| 6,544,171 B2 | 4/2003 | Beetz et al. | |
| 6,558,347 B1 | 5/2003 | Jhuboo et al. | |
| 6,572,604 B1 | 6/2003 | Platt et al. | |
| 6,622,542 B2 | 9/2003 | Derek et al. | |
| 6,635,033 B1 * | 10/2003 | Hill | A61M 5/16813 604/249 |
| 6,648,861 B2 | 11/2003 | Platt et al. | |
| 6,692,241 B2 * | 2/2004 | Watanabe | A61M 5/14228 417/477.2 |
| 6,733,476 B2 | 5/2004 | Christenson et al. | |
| 6,742,992 B2 | 6/2004 | Davis | |
| 6,749,587 B2 | 6/2004 | Flaherty | |
| 6,768,425 B2 | 7/2004 | Flaherty et al. | |
| 6,788,199 B2 | 9/2004 | Crabtree et al. | |

(56) References Cited

U.S. PATENT DOCUMENTS

| | | |
|---|---|---|
| 6,790,198 B1 | 9/2004 | White et al. |
| 6,902,549 B2 | 6/2005 | Marmaropoulos et al. |
| 6,942,473 B2 | 9/2005 | Abrahamson et al. |
| 7,018,361 B2 | 3/2006 | Gillespie, Jr. et al. |
| 7,022,075 B2 | 4/2006 | Grunwald et al. |
| 7,048,720 B1 | 5/2006 | Thorne, Jr. et al. |
| 7,059,840 B2 | 6/2006 | Corwin et al. |
| 7,122,026 B2 | 10/2006 | Rogers et al. |
| 7,131,966 B1 | 11/2006 | Tamari |
| 7,163,385 B2 | 1/2007 | Gharib et al. |
| 7,347,836 B2 | 3/2008 | Peterson et al. |
| 7,525,432 B2 | 4/2009 | Jackson |
| 7,556,481 B2 | 7/2009 | Moubayed |
| 7,611,498 B2 * | 11/2009 | Hasler ............... A61M 5/14228 604/131 |
| 7,645,258 B2 | 1/2010 | White et al. |
| 7,654,976 B2 | 2/2010 | Peterson et al. |
| 7,695,255 B2 | 4/2010 | Ben-Shalom et al. |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |
| 8,025,634 B1 | 9/2011 | Moubayed et al. |
| 8,029,253 B2 * | 10/2011 | Rotem ............... A61M 5/14228 417/478 |
| 8,105,282 B2 * | 1/2012 | Susi .................. A61M 5/14228 600/411 |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,469,932 B2 * | 6/2013 | Susi .................... F04B 43/082 604/250 |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 * | 11/2002 | Morris ............... A61M 5/14228 604/250 |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0112001 A1 | 5/2005 | Bahnen et al. |
| 2005/0171501 A1 | 8/2005 | Kelly |
| 2005/0191196 A1 | 9/2005 | Tanner et al. |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173419 A1 * | 8/2006 | Malcolm ........... A61M 5/16827 604/246 |
| 2006/0213249 A1 | 9/2006 | Uram et al. |
| 2007/0032098 A1 | 2/2007 | Bowles et al. |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0135866 A1 | 6/2007 | Baker et al. |
| 2007/0154336 A1 | 7/2007 | Miyazaki et al. |
| 2007/0217931 A1 | 9/2007 | Estes et al. |
| 2007/0269324 A1 * | 11/2007 | Goldor ............... A61M 5/14228 417/474 |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 * | 4/2008 | Ben-Shalom ...... A61M 5/14228 417/474 |
| 2008/0144560 A1 | 6/2008 | Jia et al. |
| 2008/0145249 A1 | 6/2008 | Smisson et al. |
| 2008/0146995 A1 | 6/2008 | Smisson et al. |
| 2008/0275307 A1 | 11/2008 | Poschmann |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1 * | 9/2009 | Rotem ............... A61M 5/14228 604/151 |
| 2009/0240201 A1 | 9/2009 | Rotem et al. |
| 2009/0270810 A1 | 10/2009 | DeBelser et al. |
| 2009/0300507 A1 | 12/2009 | Raghavan et al. |
| 2009/0317268 A1 * | 12/2009 | Rotem .................... F04B 43/12 417/53 |
| 2010/0016781 A1 | 1/2010 | Nakayama et al. |
| 2010/0036322 A1 | 2/2010 | Rotem |
| 2010/0082001 A1 | 4/2010 | Beck et al. |
| 2010/0168545 A1 | 7/2010 | Kamath et al. |
| 2010/0211002 A1 | 8/2010 | Davis |
| 2010/0228223 A1 | 9/2010 | Williams et al. |
| 2010/0234708 A1 | 9/2010 | Buck et al. |
| 2010/0279652 A1 | 11/2010 | Sharp et al. |
| 2011/0148624 A1 | 6/2011 | Eaton et al. |
| 2011/0152772 A1 * | 6/2011 | Rotem ............... A61M 5/14228 604/153 |
| 2011/0152831 A1 * | 6/2011 | Rotem ............... A61M 5/14228 604/506 |
| 2011/0167133 A1 | 7/2011 | Jain |
| 2011/0251856 A1 | 10/2011 | Maus et al. |
| 2011/0264043 A1 | 10/2011 | Kotnik et al. |
| 2011/0276000 A1 | 11/2011 | Stringham |
| 2011/0282291 A1 | 11/2011 | Ciccone |
| 2011/0318208 A1 * | 12/2011 | Goldor ............... A61M 5/14228 417/477.1 |
| 2012/0059389 A1 | 3/2012 | Larson et al. |
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0279370 A1 | 10/2013 | Eitan et al. |
| 2013/0345623 A1 | 12/2013 | Kopperschmidt et al. |
| 2014/0005631 A1 | 1/2014 | Rotem et al. |

(56) References Cited

U.S. PATENT DOCUMENTS

| | | |
|---|---|---|
| 2014/0119954 A1 | 5/2014 | Schweitzer et al. |
| 2014/0197824 A1 | 7/2014 | Gillespie et al. |
| 2014/0222377 A1 | 8/2014 | Bitan et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0038187 A1 | 2/2015 | Ho et al. |
| 2015/0073338 A1 | 3/2015 | Waldhoff et al. |
| 2015/0105726 A1 | 4/2015 | Qi et al. |
| 2015/0137988 A1 | 5/2015 | Gravenstein et al. |
| 2015/0141955 A1 | 5/2015 | Ruchti et al. |
| 2015/0172921 A1 | 6/2015 | Wang et al. |
| 2015/0182694 A1 | 7/2015 | Rosinko |
| 2015/0192120 A1 | 7/2015 | Rotem et al. |

FOREIGN PATENT DOCUMENTS

| | | |
|---|---|---|
| EP | 0215249 A1 | 3/1987 |
| EP | 0225158 A2 | 6/1987 |
| EP | 0315312 A1 | 5/1989 |
| EP | 0429866 A1 | 6/1991 |
| EP | 0483794 A1 | 5/1992 |
| EP | 0858812 A2 | 8/1998 |
| EP | 1031358 A1 | 8/2000 |
| EP | 1350955 A2 | 10/2003 |
| EP | 1557186 | 7/2005 |
| EP | 1611834 A2 | 1/2006 |
| EP | 1485149 B1 | 7/2008 |
| FR | 2632529 A | 12/1989 |
| FR | 2632529 A1 | 12/1989 |
| FR | 2753236 A1 | 3/1998 |
| JP | 60043188 A | 3/1985 |
| JP | 6-169992 A | 6/1994 |
| JP | 2002-57738 A | 2/2002 |
| JP | 2004141418 A | 5/2004 |
| WO | 8400691 A1 | 3/1984 |
| WO | 9116933 A1 | 11/1991 |
| WO | 9325816 A1 | 12/1993 |
| WO | 9408647 A1 | 4/1994 |
| WO | 9603168 A1 | 2/1996 |
| WO | 9630679 A1 | 10/1996 |
| WO | 9734084 A1 | 9/1997 |
| WO | 9804301 A1 | 2/1998 |
| WO | 9813080 A2 | 4/1998 |
| WO | 9847551 A1 | 10/1998 |
| WO | 99/58178 A1 | 11/1999 |
| WO | 0139816 A2 | 6/2001 |
| WO | 0165232 A1 | 9/2001 |
| WO | 0236044 A2 | 5/2002 |
| WO | 0238204 A2 | 5/2002 |
| WO | 0249509 A2 | 6/2002 |
| WO | 02068015 A2 | 9/2002 |
| WO | 03027503 A1 | 4/2003 |
| WO | 03080158 A1 | 10/2003 |
| WO | 2004070548 A2 | 8/2004 |
| WO | 2004093648 A2 | 11/2004 |
| WO | 2005089263 A2 | 9/2005 |
| WO | 2006/056986 A1 | 6/2006 |
| WO | 2007133259 A1 | 11/2007 |
| WO | 2008036658 A2 | 3/2008 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |
| WO | 2010053702 A1 | 5/2010 |
| WO | 2010053703 A1 | 5/2010 |
| WO | 2010091313 A2 | 8/2010 |
| WO | 2011128850 A2 | 10/2011 |
| WO | 2012095827 A1 | 7/2012 |
| WO | 2012095829 A2 | 7/2012 |
| WO | 2013001425 A2 | 1/2013 |
| WO | 2013/028704 A1 | 2/2013 |
| WO | 2013/090748 A1 | 6/2013 |

OTHER PUBLICATIONS

International Application PCT/IL2007/001398 Search Report dated Jun. 11, 2008.
International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
International Application PCT/IL2003/000947 Search Report dated Mar. 3, 2004.
Chinese Patent Application No. 200580045471.3 "Finger-type peristaltic pump" Official Action dated Jul. 18, 2008.
U.S. Appl. No. 09/125,438 Official dated May 3, 1999.
U.S. Appl. No. 09/125,438 Official dated Jul. 15, 1999.
European Application No. 05810500.8 Official Action dated Jul. 6, 2009.
International Application PCT/IL1997/000289 Search report dated Jan. 27, 1998.
International Application PCT/IL1997/000290 Search Report dated Jan. 27, 1998.
Honeywell Sensing and Control, "FSS1500NSB force sensor", Golden Valley, Minnesota, USA, 1998-2004 http://sccatalog.honeywell.com/imc/printfriendly.asp?FAM=force&PN=FSS1500NSB.
Chinese Patent Application No. 200780041966.8 Official Action dated Jul. 13, 2010.
U.S. Appl. No. 11/791,599 Official dated Aug. 19, 2010.
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance issued Apr. 29, 2013 (14 pages).
U.S. Appl. No. 12/514,310 Official Action (Non-Final) dated Jul. 21, 2011 (8 pages).

(56) References Cited

OTHER PUBLICATIONS

U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance issued Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance issued Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance issued Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance issued Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
Honeywell Sensing and Control, "FSSI500NSB force sensor", Golden Valley, Minnesota, USA, 1998-2004 http://sccatalog.honeywell.com/imc/printfriendly.asp?FAM~force&PN~FSSI500NSB (5 pages).
International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).
International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).
International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance issued Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance issued Apr. 19, 2013 (6 pages).
U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).

(56) References Cited

OTHER PUBLICATIONS

Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, issued Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance issued Jul. 11, 2012 (5 pages).
U.S. Appl. No. 12/464,202 Official Action dated Oct. 3, 2011.
U.S. Appl. No. 12/463,399 Official Action dated Jul. 21, 2011.
U.S. Appl. No. 12/514,310 Official Action dated Jul. 21, 2011.
U.S. Appl. No. 12/644,027 Official Action dated Apr. 28, 2011.
U.S. Appl. No. 11/791,599 Official Action dated Mar. 31, 2011.
European Patent Application # 10192477.7 Search Report dated May 10, 2011.
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance issued Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).
European Application No. 05810500.8 Official Action dated Nov. 3, 2014 (5 pages).
European Application No. 05810500.8 Response to Official Action dated Nov. 3, 2014, submitted Mar. 9, 2015 (31 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).
U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).
U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
European Application No. 11768544.6 Response to Official Action dated Dec. 2, 2014, submitted May 29, 2015 (12 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jan. 23, 2015 (24 pages).
U.S. Appl. No. 13/978,538 Response to Official Action (Non-Final) dated Jan. 23, 2015, submitted May 21, 2015 (13 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
European Application No. 12805094.5 Supplementary European Search Report dated Jun. 30, 2015 (14 pages).
U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).
PCT Appl. No. PCT/IB14/62106 International Search Report and Written Opinion dated Feb. 24, 2015 (8 pages).
PCT Appl. No. PCT/IB15/50873 International Search Report and Written Opinion dated Jun. 25, 2015 (8 pages).

\* cited by examiner

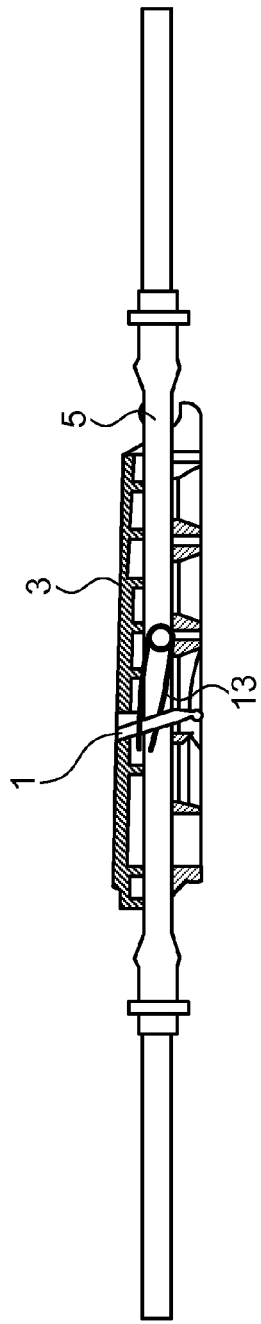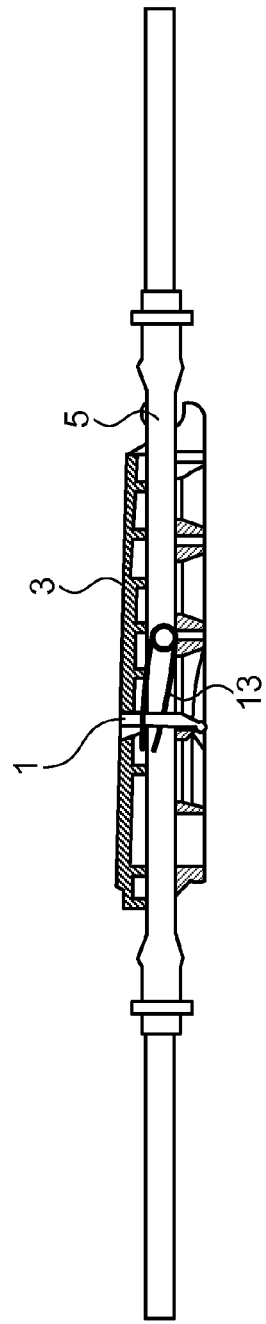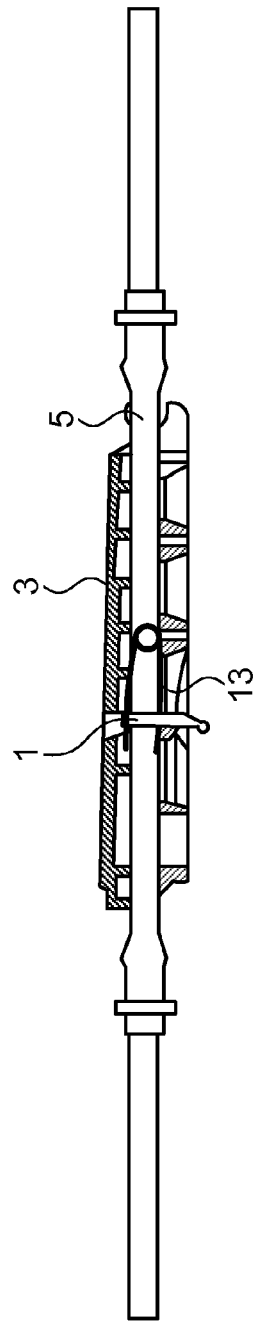

MS - VALVE OPEN & SECURED

MS - VALVE OPEN

MS - VALVE CLOSED

ANTI-FREE FLOW MECHANISM

FIELD OF THE INVENTION

The present invention generally relates to an anti-free flow mechanism for a finger-type peristaltic infusion pump.

BACKGROUND OF THE INVENTION

An infusion pump infuses fluids, medication or nutrients into a patient's circulatory system. It is generally used intravenously, although subcutaneous, arterial and epidural infusions are occasionally used.

Infusion pumps can administer fluids in ways that would be impractically expensive or unreliable if performed manually by nursing staff. For example, they can administer as little as 0.1 mL per hour injections, injections every minute, injections with repeated boluses requested by the patient, up to maximum number per hour, or fluids whose volumes vary by the time of day. Because they can also produce quite high but controlled pressures, they can inject controlled amounts of fluids e.g., subcutaneously or epidurally.

Among other safety features available on some pumps, anti-free flow mechanisms and anti-free-flow devices prevent blood from draining from the patient, or infusate from freely entering the patient, when the infusion pump is being set up.

Various approaches were taken in the literature to ensure anti-free-flow in those pumps. Hence for example, U.S. Pat. No. 6,261,262 discloses a peristaltic pump with housing, a pump head in the housing, and a receiving path defined along housing and pump head for receiving tubing. Nevertheless, an effective anti-free flow provided in a passive mechanical interface (MS) which integrally accommodates a portion of the flexible infusion-tube wherein a flow of infusion fluid is provided is still a long felt need.

SUMMARY OF THE INVENTION

It is thus the object of the present invention to provide an anti-free flow mechanism for a finger-type peristaltic infusion pump (DDS); the mechanism comprising (i) a passive mechanical interface (MS) which integrally accommodates a portion of the flexible infusion-tube, and (ii) an anti-free flow valve (AFFV) which is a spring-activated latch incorporated within the MS. The maneuverable latch is secured in the MS either in a CLOSED or OPEN configuration. In its CLOSED configuration no flow is provided, and vice versa, in its OPEN configuration, a free flow is facilitated. The anti-free flow mechanism is configured in a manner such that when the MS is not properly mounted in said DDS, the AFFV is automatically actuated via a plurality of springs, and especially a set of one or more integrated springs, to its CLOSED configuration, and vice versa: It is configured in a manner such that when the MS is properly mounted in said DDS, the latch is adapted to be automatically switched to the OPEN configuration. The terms 'AFFV' and 'spring-activated latch' are used hereinafter interchangeably.

Another object of the present invention is to provide an anti-free flow mechanism as defined above, wherein the AFFV is adapted to be manually switched to a secured-OPEN configuration when the MS is not mounted in said DDS. The configuration-switch is possibly provided by applying a continuous pressure on the AFFV, and vice versa. Immediately after stopping to press, the AFFV is switched to its CLOSED configuration. Another object of the present invention is to provide an anti-free flow mechanism as defined above, wherein the AFFV is adapted to be manually switched to its OPEN configuration when the MS is not mounted in the DDS. The switching is provided possibly by applying a single tilting press on the AFFV. The OPEN configuration is possibly followed by either (i) switching said AFFV to its CLOSED configuration or (ii) switching the AFFV to its secured-OPEN configuration.

Another object of the present invention is to provide an anti-free flow mechanism as defined above, wherein the AFFV is adapted to be automatically switched to its CLOSED configuration when the MS is switched-out of the DDS, regardless of the initial OPEN/CLOSED configuration of the AFFV (when the MS was mounted in said DDS).

Still another object of the present invention is to provide an anti-free flow mechanism as defined above, wherein the AFFV is especially adapted to be manually switched to its various OPEN/CLOSED configurations by one hand.

A last object of the present invention is to provide a method for providing an anti-free flow mechanism in a finger-type peristaltic infusion pump (DDS). The method comprises steps as follows:

(a) obtaining an anti-free flow mechanism for a finger-type peristaltic infusion pump (DDS); said mechanism comprising (i) a passive mechanical interface (MS) which integrally accommodates a portion of the flexible infusion-tube, and (ii) an anti-free flow valve (AFFV) which is a spring-activated latch incorporated within said MS. Said maneuverable latch is secured in said MS either in CLOSED or OPEN configurations. In its CLOSED configuration no flow is provided, and vice versa: In its OPEN configuration, a free flow is facilitated. Said anti-free flow mechanism is configured in a manner such that when the MS is not properly mounted in the DDS, the AFFV is automatically actuated via a plurality of springs, and especially a set of one or more integrated springs, to its CLOSED configuration; and vice versa: It is configured in a manner such that when said MS is properly mounted in said DDS, said latch is adapted to be automatically switched to said OPEN configuration; and (b) one or more of the following steps:
(i) manually switching the AFFV to a TEMPORARILY-OPEN configuration when the MS is not mounted in the DDS. The switching is provided possibly by applying a continuous pressure on said AFFV, and vice versa. Immediately after stopping to press, the AFFV is switched to its CLOSED configuration;
(ii) automatically switching said AFFV to its CLOSED configuration when the MS is switched-out of the DDS, regardless of the initial SECURED-OPEN/TEMPORARILY-OPEN/CLOSED configuration of said AFFV, when the MS was mounted in said DDS);
and,
(iii) manually switching the AFFV to its various OPEN/CLOSED configurations by one hand, while the MS is not mounted in the DDS.

BRIEF DESCRIPTION OF THE FIGURES

In order to understand the invention and to see how it may be implemented in practice, a plurality of preferred embodiments will now be described, by way of non-limiting example only, with reference to the accompanying drawing, in which FIG. 1 schematically illustrates a cross-section of a DDS-MS with anti-free flow mechanism according to one embodiment of the present invention;

FIGS. 4a-4c schematically illustrate cross-sections of an anti-free flow mechanism in various OPEN/CLOSED configurations with a view of both AFFV and springs, according to one embodiment of the present invention; and, FIGS. 5a-5c schematically illustrate simplified cross-sections of an anti-free flow mechanism in its various OPEN/CLOSED configurations.

DETAILED DESCRIPTION OF THE INVENTION

The following description is provided so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide an anti-free flow mechanism for a finger-type peristaltic infusion pump.

The term 'plurality' refers hereinafter to any integer number equal to or higher than 1, e.g., 2, 4 etc.

An anti-free flow mechanism is incorporated within a passive mechanical interface. The interface is adapted for mounting of a flexible infusion tube in a finger-type peristaltic infusion pump in a reversible yet secured manner.

The present invention discloses a passive mechanical interface, denoted hereinafter by the term 'MS', being a mechanical interface of the set of tubing to the DDS, that has no moving parts or static members being an integral part of the aforesaid pumping mechanism or sensors thereof, e.g., pistons, hinges, cams, wheels, sealing membranes, gaskets, etc. The MS is interlaced with an integrated anti-free flow mechanism, useful for mounting a flexible infusion tube to a finger-type peristaltic infusion pump, so as to provide a uni-directional or bi-directional flow, provided by the pump solely in a predetermined direction of an infusion.

The MS reversibly yet securely mounts the tube in a predetermined 3D orientation so it is facing the pumping mechanism and various sensors of the infusion pump. The MS hence comprises a mechanical conductor for the set of tubing that acts as an interface of said tubing to a pump and an anti-free flow valve (AFFV).

Figure 1:
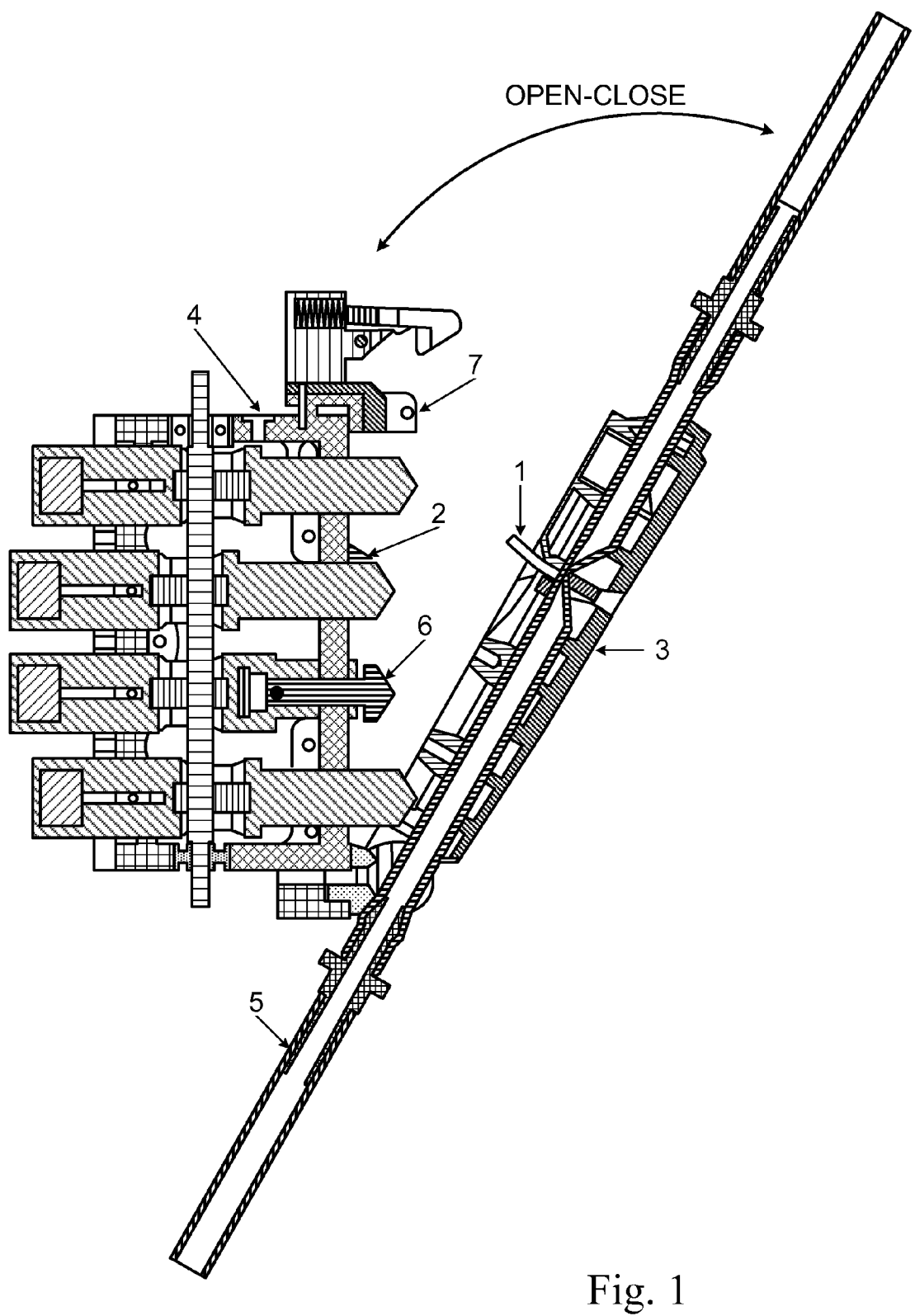

Reference is now made to FIG. 1, schematically illustrating a cross section of a DDS and anti-free flow mechanism according to one embodiment of the present invention. A passive mechanical interface (MS, 3) is mounted in a finger-type peristaltic infusion pump (4) so that pressing fingers (6) and sensors (here, bubble detector, 7) are perfectly oriented towards a flexible infusion-tube (5) accommodated in said MS. The anti-free flow mechanism comprises an anti-free flow latch (1), valve or shutoff located in the MS (3), facing an AFFV-activating member (2) located in the DDS. The AFFV is now in its CLOSED configuration and infused fluid is not flowing via tube (5). By mounting MS in the DDS (See Open-Close arrow), AFFV is pressed against the AFFV-activating member (2) and AFFV is automatically switched on to its OPEN configuration, and flow of the infused fluid is allowed via tube (5).

Figures 2A, 2B, 2C:
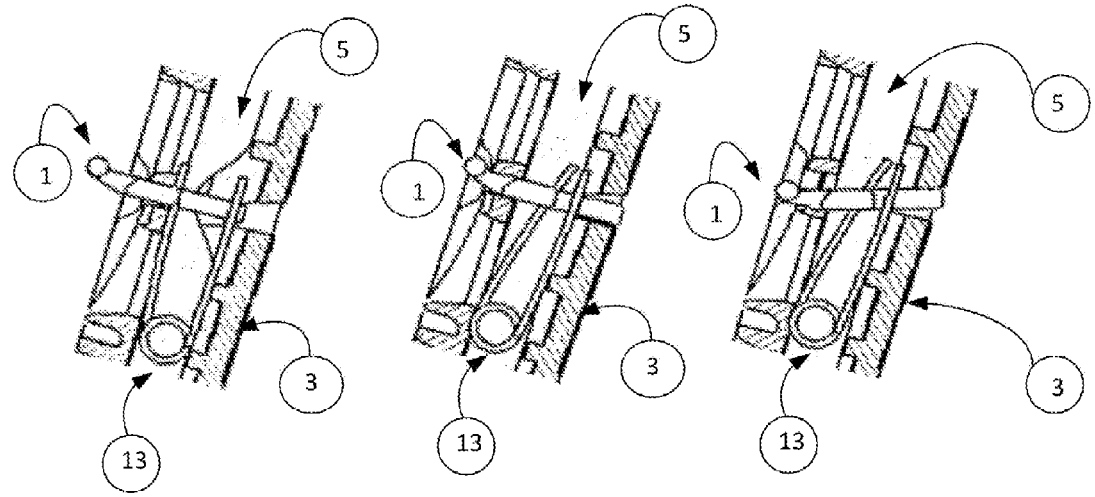
FIGS. 2a-2c schematically illustrate detailed cross-sections of an MS with AFFV in various OPEN/CLOSED configurations according to one embodiment of the present invention.

Reference is now made to FIGS. 2a-2c, schematically illustrating an AFFV mechanism in three different OPEN/CLOSED configurations. Those schemes present both valves and springs oriented in various configurations.

Figure 3:
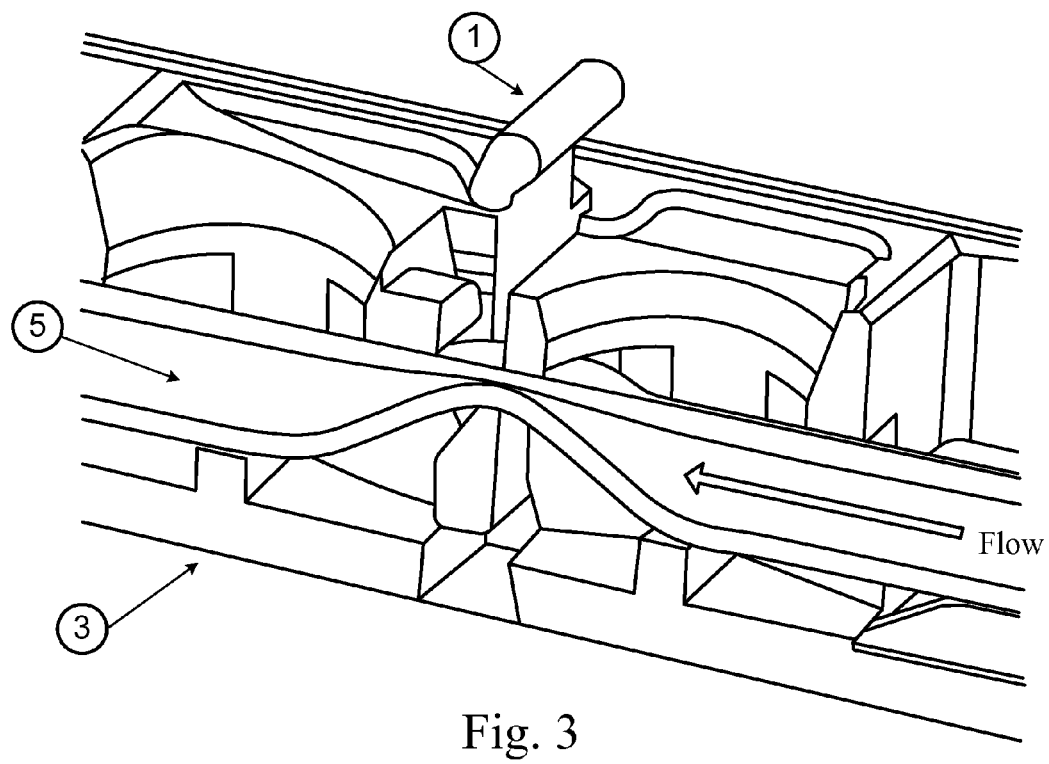
FIG. 3 schematically illustrates cross-sections of an anti-free flow mechanism in a CLOSED configuration.

Reference is now made to FIG. 3, schematically illustrating the anti-free flow mechanism according to one embodiment of the present invention, being temporarily in its CLOSED configuration. MS (3) is accommodating flexible infusion tube (5).

Reference is now made to FIGS. 4a-4c, schematically presenting a various OPEN/CLOSED configurations of the anti-free flow mechanism. FIG. 4a illustrates the MS wherein AFFV is in its OPEN and secured configuration. The MS (3) here accommodates an infusion tube (5), wherein the AFFV (1) is in connection to a plurality (e.g., 1-4) of retrieving springs (13). FIG. 4b illustrates the MS wherein the AFFV is in its OPEN configuration. FIG. 4c illustrates the MS wherein the AFFV is in its CLOSED configuration.

Figure 5A:
Figure 5B:
Figure 5C:
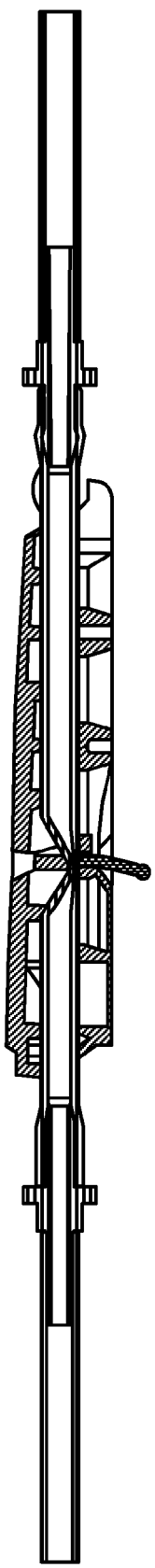

Reference is now made to FIGS. 5a-c, schematically presenting various OPEN/CLOSED configurations of the anti-free flow mechanism without showing the spring members. FIG. 5a presents the MS wherein the AFFV is in its OPEN and secured configuration. FIG. 5b illustrates the MS wherein the AFFV is in its OPEN configuration. FIG. 5c illustrates the MS wherein AFFV is in its CLOSED configuration.

The invention claimed is:

1. A method for pumping a fluid, comprising:
   (a) providing a passive mechanical interface, which contains a portion of a flexible infusion tube for conveying the fluid through a finger-type peristaltic pump having multiple fingers, and which movably holds a latch, wherein prior to mounting of the passive mechanical interface onto the finger-type peristaltic pump, the latch assumes a closed configuration in which said latch compresses the infusion tube, wherein the latch protrudes from the passive mechanical interface in the closed configuration;
   (b) mounting the passive mechanical interface onto the finger-type peristaltic pump thereby pressing the latch of the passive mechanical interface against an activating member so as to assume an open configuration of the infusion tube so that one or more of the multiple fingers press against the infusion tube and so that the latch engages the activating member between the multiple fingers in the finger-type peristaltic pump, which causes the latch to switch automatically to the open configuration in which the fluid is allowed to flow through the infusion tube; and
   (c) manually switching and securing the latch in the open configuration by pressing and tilting the latch into the passive mechanical interface.

2. A method for pumping a fluid, comprising:
   (a) providing a passive mechanical interface, which contains a portion of a flexible infusion tube for conveying the fluid through a finger-type peristaltic pump having multiple fingers, and wherein the passive mechanical interface movably holds a latch and a spring to activate a closed configuration of the latch, wherein prior to mounting of the passive mechanical interface onto the finger-type peristaltic pump, the latch assumes the closed configuration in which said latch compresses the infusion tube; and
   (b) mounting the passive mechanical interface onto the finger-type peristaltic pump so that one or more of the multiple fingers press against the infusion tube and so that the latch engages an activating member between the multiple fingers in the finger-type peristaltic pump, which causes the latch to switch automatically to an open configuration in which the fluid is allowed to flow through the infusion tube;
   wherein the spring is configured to return the passive mechanical interface to the closed configuration upon removal of the passive mechanical interface from the finger-type peristaltic pump, regardless of whether the passive mechanical interface was open or closed when mounted onto the finger-type peristaltic pump.

* * * * *